(12) United States Patent
Meyer et al.

(10) Patent No.: US 7,076,398 B2
(45) Date of Patent: Jul. 11, 2006

(54) METHOD FOR DETERMINING VACUUM PRODUCER SYSTEM PARAMETERS AND PERFORMANCE SPECIFICATIONS

(75) Inventors: Robert A. Meyer, Spearfish, SD (US); James Isaac Meyer, Spearfish, SD (US)

(73) Assignee: RAMVAC Dental Products, Inc., Spearfish, SD (US)

( * ) Notice: Subject to any disclaimer, the term of this patent is extended or adjusted under 35 U.S.C. 154(b) by 35 days.

(21) Appl. No.: 10/994,258

(22) Filed: Nov. 23, 2004

(65) Prior Publication Data

US 2005/0075838 A1    Apr. 7, 2005

Related U.S. Application Data

(63) Continuation-in-part of application No. 10/385,429, filed on Mar. 12, 2003, now Pat. No. 6,925,886.

(51) Int. Cl.
G06F 19/00   (2006.01)

(52) U.S. Cl. ......................... 702/182; 73/1.85

(58) Field of Classification Search ................ 702/182, 702/23, 41, 45, 114, 138, 183, 185; 73/1.85, 73/40.7; 95/101, 102, 175
See application file for complete search history.

(56) References Cited

U.S. PATENT DOCUMENTS

| | | | |
|---|---|---|---|
| 4,894,145 A | 1/1990 | Jensen | |
| 5,407,465 A | 4/1995 | Schaub et al. | |
| 5,485,754 A | 1/1996 | Harpster | |
| 5,625,141 A * | 4/1997 | Mahoney et al. | ............ 73/40.7 |
| 5,637,809 A | 6/1997 | Traina et al. | |
| 5,752,411 A | 5/1998 | Harpster | |
| 6,325,624 B1 | 12/2001 | Kutsch et al. | |
| 6,347,649 B1 | 2/2002 | Pope et al. | |
| 6,406,294 B1 | 6/2002 | Bell | |
| 2005/0005683 A1 * | 1/2005 | Wolford et al. | ............ 73/49.2 |

OTHER PUBLICATIONS

Texas A&M Statistics Website http://stat.tamu.edu/stat30x/notes/node66.html entitled "The Binomial Distribution", 2 pages, Nov. 13, 1996.

* cited by examiner

*Primary Examiner*—Edward Raymond
(74) *Attorney, Agent, or Firm*—Nixon & Vanderhye P.C.

(57) ABSTRACT

A vacuum-strength measurement device is utilized to determine vacuum producer system performance specifications and system parameters. A flow ability factor can be determined that represents the effect of system piping and usage area equipment on performance. With the flow ability factor, a vacuum strength requirement can be determined to effect a target vacuum performance. For system design, design parameters can be established based on a relationship between a desired flow ability factor and an amount of vacuum strength required to match target vacuum performance.

14 Claims, 3 Drawing Sheets

Convert with Chart
At sea level,
2.6" Hg = 9.4 SCFM

| Flowcheck Gauge [in Hg] | Air Flow [SCFM] Altitude | | | |
|---|---|---|---|---|
| | Sea Level | 2000 ft | 4000 ft | 8000 ft |
| 0.0 | 0.0 | 0.0 | 0.0 | 0.0 |
| 0.2 | 2.6 | 2.5 | 2.4 | 2.2 |
| 0.4 | 3.7 | 3.6 | 3.4 | 3.2 |
| 0.6 | 4.5 | 4.3 | 4.2 | 3.9 |
| 0.8 | 5.2 | 5.0 | 4.8 | 4.5 |
| 1.0 | 5.8 | 5.6 | 5.4 | 5.0 |
| 1.2 | 6.4 | 6.2 | 5.9 | 5.5 |
| 1.4 | 6.9 | 6.6 | 6.4 | 5.9 |
| 1.6 | 7.4 | 7.1 | 6.8 | 6.3 |
| 1.8 | 7.8 | 7.5 | 7.2 | 6.7 |
| 2.0 | 8.3 | 7.9 | 7.6 | 7.1 |
| 2.2 | 8.7 | 8.3 | 8.0 | 7.4 |
| 2.4 | 9.1 | 8.7 | 8.4 | 7.7 |
| 2.6 | 9.4 | 9.1 | 8.7 | 8.1 |
| 2.8 | 9.8 | 9.4 | 9.0 | 8.4 |
| 3.0 | 10.1 | 9.7 | 9.4 | 8.7 |
| 3.2 | 10.5 | 10.0 | 9.7 | 8.9 |
| 3.4 | 10.8 | 10.4 | 10.0 | 9.2 |
| 3.6 | 11.1 | 10.7 | 10.2 | 9.5 |
| 3.8 | 11.4 | 10.9 | 10.5 | 9.7 |
| 4.0 | 11.7 | 11.2 | 10.8 | 10.0 |
| 4.2 | 12.0 | 11.5 | 11.1 | 10.3 |
| 4.4 | 12.3 | 11.8 | 11.3 | 10.5 |
| 4.6 | 12.5 | 12.0 | 11.6 | 10.7 |
| 4.8 | 12.8 | 12.3 | 11.8 | 11.0 |
| 5.0 | 13.1 | 12.6 | 12.1 | 11.2 |

METHOD FOR DETERMINING VACUUM PRODUCER SYSTEM PARAMETERS AND PERFORMANCE SPECIFICATIONS

CROSS-REFERENCES TO RELATED APPLICATIONS

This application is a continuation-in-part (CIP) of U.S. patent application Ser. No. 10/385,429, filed Mar. 12, 2003 now U.S. Pat. No. 6,925,886, the entire content of which is herein incorporated by reference.

STATEMENT REGARDING FEDERALLY SPONSORED RESEARCH OR DEVELOPMENT (NOT APPLICABLE)

BACKGROUND OF THE INVENTION

The present invention relates to a method for determining vacuum producer system parameters and performance specifications and, more particularly, to such a method enabling system design and/or evaluation.

In an environment housing multiple dental treatment rooms, typically a single vacuum source or vacuum producer system provides vacuum air flow for an entire facility or multiple rooms in the facility. The vacuum producer system drives vacuum air flow through vacuum devices such as a high volume evacuator (HVE) vacuum tip. Such a tip is typically placed in a dental patient's mouth to remove fluid and debris from the patient's mouth during a dental treatment.

A vacuum flow measurement device is disclosed in the above-noted related application, of which this application is a continuation-in-part. The flow measurement device disclosed therein enables the measurement of a vacuum pump performance generating the vacuum air flow at the HVE tip without adding flow restriction to the system.

It would be desirable to utilize such a flow measurement device and/or a vacuum gauge to determine vacuum producer system parameters and/or performance specifications to facilitate system design and/or evaluate system performance.

BRIEF SUMMARY OF THE INVENTION

It is thus an object of the invention to provide a method of determining vacuum producer system parameters and/or performance specifications using a vacuum strength measurement device. Although the system will be described in conjunction with an application to a dental treatment facility, the method of the invention is equally applicable to any vacuum producer system providing vacuum air flow for a plurality of vacuum devices.

In an exemplary embodiment of the invention, a method of determining vacuum producer system parameters utilizes a vacuum strength measurement device, which may comprise the vacuum flow measurement device of the noted related application and/or a vacuum gauge, where the vacuum producer system serves a plurality of vacuum devices. The method includes the steps of (a) determining a target vacuum performance for each of the plurality of vacuum devices; and (b) determining how many of the plurality of vacuum devices have a 100% probability of being opened simultaneously. For an existing system, the method further includes (c-1) measuring vacuum performance for existing vacuum devices with the vacuum strength measurement device, (c-2) measuring sealed vacuum strength with the vacuum strength measurement device, (c-3) determining a flow ability factor based on the vacuum performance and the sealed vacuum strength, and (c-4) calculating an amount of vacuum strength required to match the target vacuum performance based on the flow ability factor determined in step (c-3). For system design, the method further includes (d-1) calculating a total flow requirement based on the target vacuum performance determined in step (a) and the number of vacuum devices determined in step (b), and (d-2) determining a relationship between (i) a desired flow ability factor based on the total flow requirement, and (ii) the amount of vacuum strength required to match the target vacuum performance.

For an existing system, step (a) may be practiced by connecting the vacuum strength measurement device to one of the vacuum devices, converting a reading from the vacuum strength measurement device using a conversion chart to determine vacuum device performance in standard cubic feet per minute (SCFM), and correlating the vacuum device performance with a desired vacuum device performance.

Step (b) is preferably practiced using a binomial distribution.

Step (c-1) may be practiced by attaching the vacuum strength measurement device with an open end, and step (c-2) may be practiced by attaching the vacuum strength measurement device with a closed end. Step (c-1) is preferably practiced to determine vacuum flow as standard cubic feet per minute (SCFM), and step (c-2) is preferably practiced to determine vacuum strength in inches of Hg.

In another exemplary embodiment of the invention, a method of determining a vacuum strength requirement for a vacuum producer system serving a plurality of vacuum devices includes the steps of (a) measuring vacuum performance for existing vacuum devices with a vacuum strength measurement device; (b) measuring sealed vacuum strength with the vacuum strength measurement device; (c) determining a flow ability factor based on the vacuum performance and the sealed vacuum strength; and (d) calculating an amount of vacuum strength required to match a target vacuum performance based on the flow ability factor determined in step (c).

BRIEF DESCRIPTION OF THE DRAWINGS

These and other aspects and advantages of the present invention will be described in detail with reference to the accompanying drawings, in which.

DETAILED DESCRIPTION OF THE INVENTION

Figure 3:
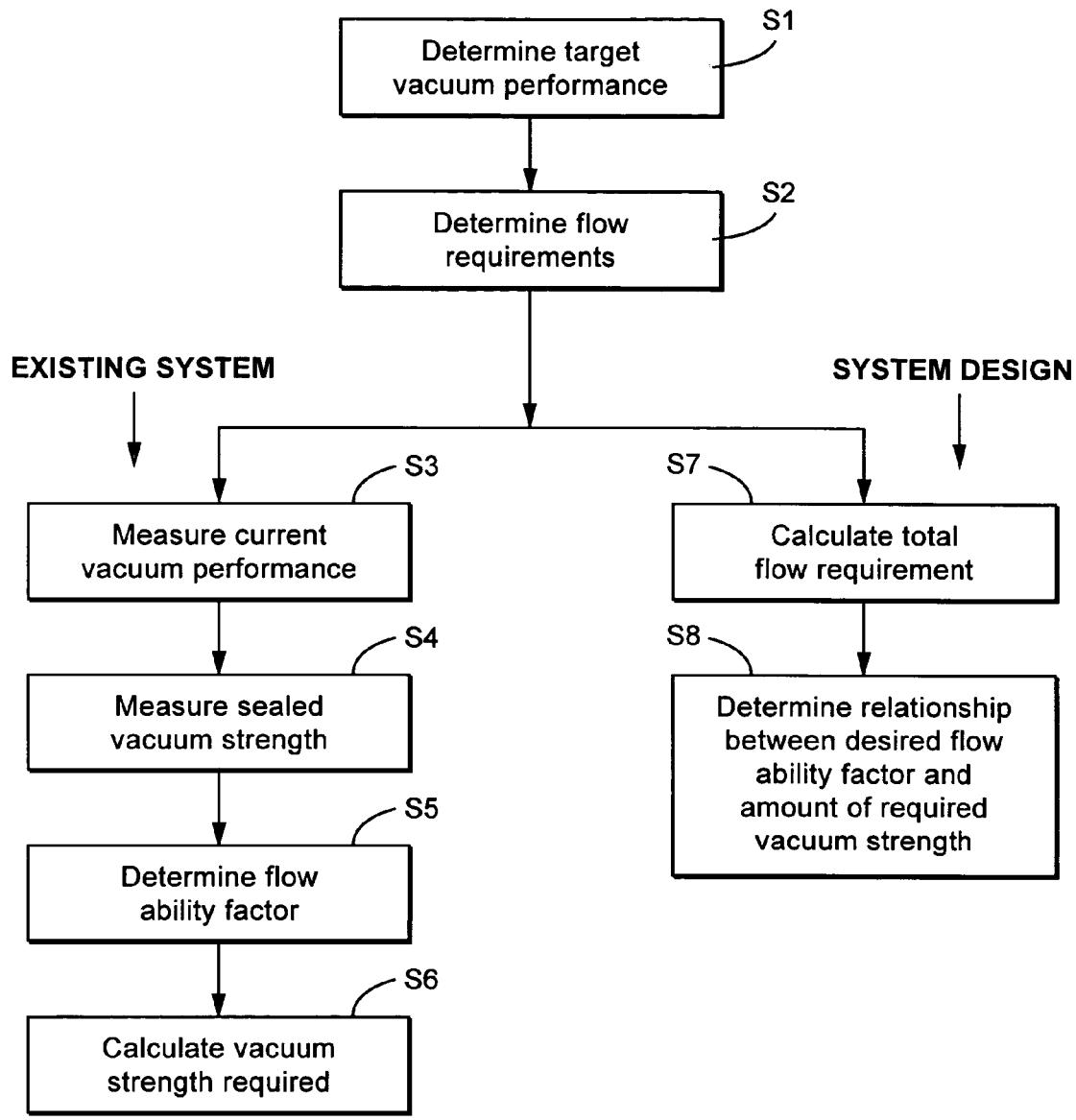
FIG. 3 is a flow chart illustrating the method of the invention.

FIG. 3 is a flow chart illustrating the method of the invention for determining vacuum producer system parameters and/or vacuum strength requirements using a vacuum strength measurement device, which may comprise the vacuum flow measurement device of the noted related application and/or a vacuum gauge. The method facilitates a determination of (i) vacuum device target performance, being how strong does the vacuum device performance need to be, (ii) vacuum device quantities, being how many vacuum devices need to be served by the vacuum producer system, and (iii) flow ability, being how much does the piping and usage area equipment (such as the treatment room in a dental facility) affect performance.

Figure 1:
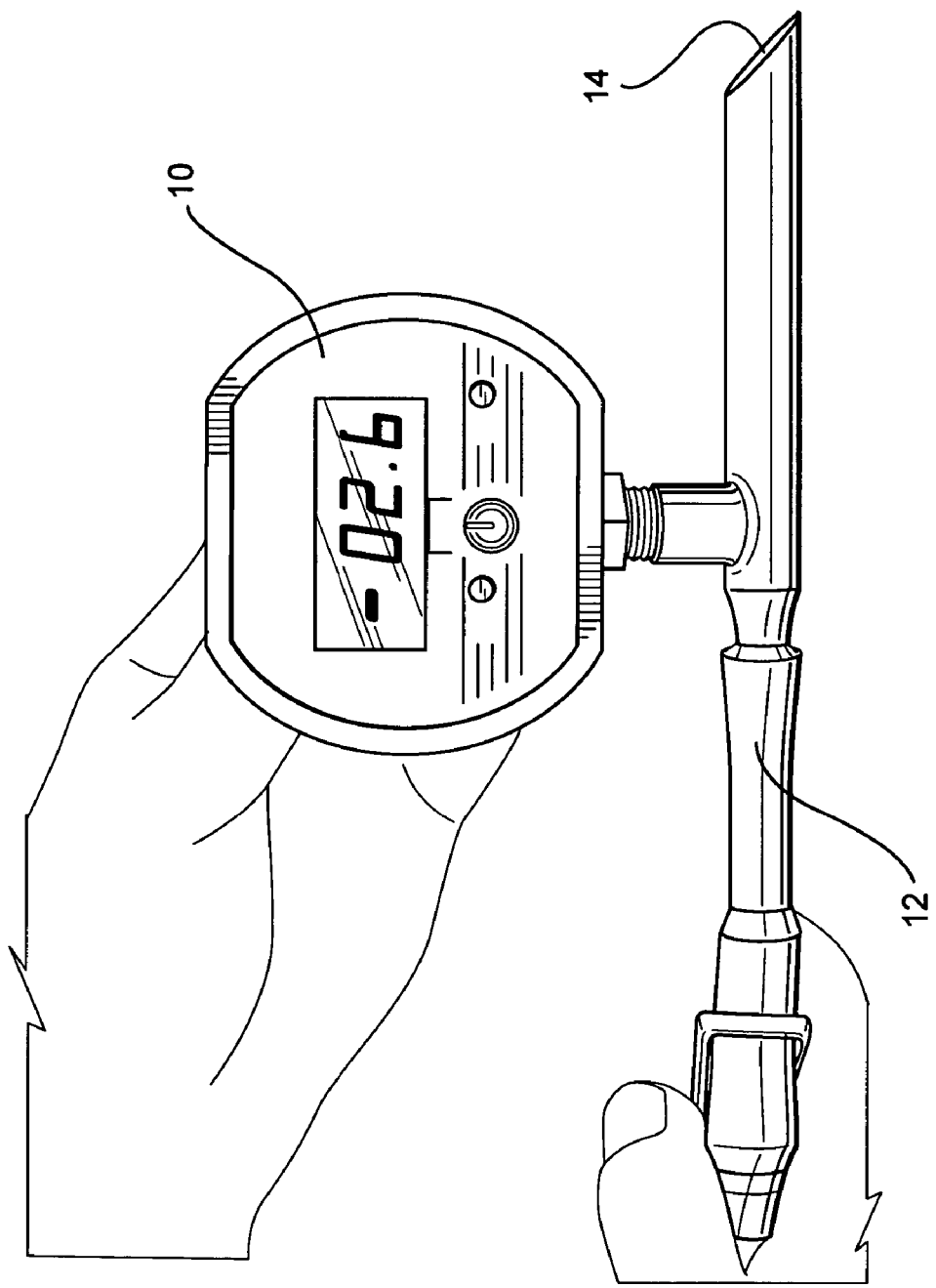
FIG. 1 shows a vacuum strength measurement device for measuring vacuum performance and for measuring sealed vacuum strength.
Figure 2:
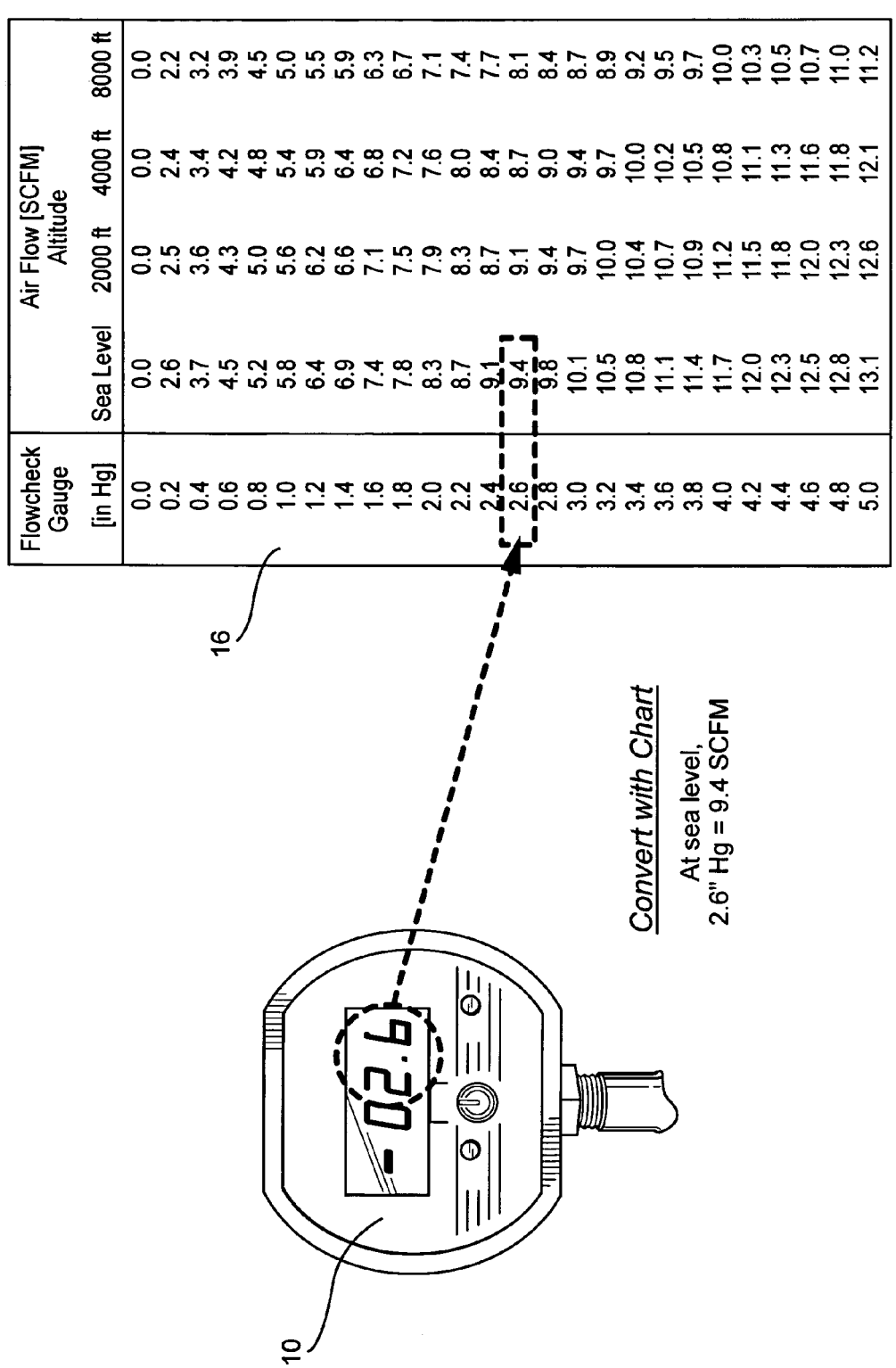
FIG. 2 shows a vacuum strength measurement device reading and a conversion chart for converting the reading into a measure of vacuum device performance in standard cubic feet per minute (SCFM)

With reference to FIG. 3, with an existing system, in order to determine target vacuum device performance (step S1), a vacuum strength measuring device such as the vacuum flow measurement device 10 of the related application is connected to an outlet 12 for one of the vacuum devices. See FIG. 1. In an open state, i.e., an end 14 of the vacuum device 10 is opened to atmosphere, with reference to FIG. 2, a reading on the vacuum flow measurement device 10 can be used to determine vacuum device performance in standard cubic feet per minute (SCFM) via a conversion chart 16.

The conversion chart was created (primarily) empirically from data collected by the applicant using an LFE (laminar flow element). The LFE was calibrated to NIST (National Institute of Standards and Technology) standards and used to measure flows at Spearfish S.D. (which is approximately 4000 ft above sea level), Chicago and New Orleans (approximately at sea level), and Lead S.D. (which is approximately 6000 ft above sea level). The 8000 ft above sea level values were extrapolated from the other data.

As shown in the conversion chart 16, air flow in SCFM varies based on the altitude in which the system is situated. Once the existing vacuum device performance in SCFM is determined, the vacuum device performance is correlated with a desired vacuum device performance. With an existing system, desired vacuum device performance can be determined based on the user's opinion of existing performance to determine how many SCFM per vacuum device or a percentage increase in SCFM per vacuum device the new system or revised system needs to provide. With system design, desired vacuum device performance can be established based on standards for the respective application, installer experience, user experience, and the like. In this context, measurements of an existing system can be used to convert qualitative target performance concepts to qualitative ones. For example, parties involved with providing a new dental vacuum system for a new facility may start without a quantitative concept of target vacuum device performance. Indeed, the party may not have thought about target performance as a "step 1" or an organized specification creating process. Their concept of vacuum system performance, typically, is limited to three categories of qualitative observations: (1) acceptable performance throughout their "old" (existing) facility or other facilities they are familiar with; (2) unacceptable performance throughout their "old" (existing) facility or other facilities they are familiar with; and/or (3) a range of performance acceptability throughout their "old" (existing) facility or other facilities they are familiar with. Measurements in any of these facilities can be used to correlate pre-existing qualitative concepts with quantitative values—the target performance for a new system.

With continued reference to FIG. 3, in step S2, the method next determines flow requirements for the vacuum producer system. That is, a determination is made concerning the number of vacuum devices to be served. In this context, using a known binomial distribution algorithm, a determination is made of how many of the vacuum devices served by the vacuum producer system have a 100% statistical probability (i.e., 99.9999%) of being opened simultaneously.

For this determination, variables include the total number of vacuum devices (e.g., the total number of chairs in a dental facility) that are planned for simultaneous occupancy by patients expected to receive treatment in which a dental vacuum will be used. For those devices, how many minutes per hour will a typical vacuum device be open. With these variables, using binomial distribution, a determination can be made as to how many of the vacuum devices served by the vacuum producer system have a 100% probability of being open simultaneously, and a total flow requirement for the system can be determined. In this context, the total flow requirement equals the number of devices 100% ON times the per unit flow. For a discussion of binomial distribution, see the statistics website for Texas A&M at http://stat.tamu.edu/stat30x/notes/node66.html, the contents of which are hereby incorporated by reference (a printout is also attached).

Once these determinations are complete, the method determines system flow ability. For an existing system, the vacuum strength measurement device is used to measure vacuum performance in SCFM and sealed vacuum strength in inches of Hg (steps S3 and S4). Using the vacuum flow measurement device of the noted related application, step S3 is practiced by attaching the vacuum flow measurement device 10 with an open end and using the conversion chart 16 shown in FIG. 2. Step S4 is practiced by attaching the vacuum flow measurement device 10 with a closed or sealed end. In this context, the vacuum flow measurement device 10 provides a reading in inches of Hg. Subsequently, the method determines the flow ability factor (K) according to:

$$K = Q/\sqrt{\Delta P}$$

where Q is the determined air flow in SCFM, and $\Delta P$ is the determined differential pressure in inches Hg. Once the flow ability factor (K) is determined, the same formula can be utilized to determine how much vacuum strength is required to produce the target performance (step S6).

For system design, it is of course impossible to determine current vacuum performance and sealed vacuum strength. Rather, a total flow requirement is calculated (step S7) based on the target vacuum performance determined initially and the number of vacuum devices determined via the binomial distribution. Subsequently, in step S8, a relationship is determined between (i) a desired flow ability factor (K) based on the total flow requirement, and (ii) the amount of vacuum strength required to match the target vacuum performance. With this relationship, the vacuum producer system piping and usage area equipment can be designed to match a target flow ability factor so that suitable vacuum strength can be incorporated into the vacuum producer system in order to match the target vacuum performance for each of the vacuum devices.

With the method of the present invention, a vacuum strength measurement device can be utilized to evaluate vacuum producer system performance and determine vacuum producer system parameters. As such, existing systems can be evaluated and new systems can be designed for optimal operating conditions.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method of determining vacuum producer system parameters using a vacuum strength measurement device, the vacuum producer system serving a plurality of vacuum devices, the method comprising:
   (a) determining a target vacuum performance for each of the plurality of vacuum devices;
   (b) determining how many of the plurality of vacuum devices have a 100% probability of being opened simultaneously; and
   (c) for an existing system,
      (c-1) measuring vacuum performance for existing vacuum devices with the vacuum strength measurement device,
      (c-2) measuring sealed vacuum strength with the vacuum strength measurement device,
      (c-3) determining a flow ability factor based on the vacuum performance and the sealed vacuum strength, and
      (c-4) calculating an amount of vacuum strength required to match the target vacuum performance based on the flow ability factor determined in step (c-3);
   (d) for system design,
      (d-1) calculating a total flow requirement based on the target vacuum performance determined in step (a) and the number of vacuum devices determined in step (b), and
      (d-2) determining a relationship between (i) a desired flow ability factor based on the total flow requirement, and (ii) the amount of vacuum strength required to match the target vacuum performance.

2. A method according to claim 1, wherein for an existing system, step (a) is practiced by connecting the vacuum strength measurement device to one of the vacuum devices, converting a reading from the vacuum strength measurement device using a conversion chart to determine vacuum device performance in standard cubic feet per minute (SCFM), and correlating the vacuum device performance with a desired vacuum device performance.

3. A method according to claim 1, wherein step (b) is practiced using a binomial distribution.

4. A method according to claim 1, wherein the vacuum strength measurement device comprises a vacuum flow measurement device, wherein step (c-1) is practiced by attaching the vacuum flow measurement device with an open end, and wherein step (c-2) is practiced by attaching the vacuum flow measurement device with a closed end.

5. A method according to claim 1, wherein step (c-1) is practiced to determine vacuum flow as standard cubic feet per minute (SCFM).

6. A method according to claim 5, wherein step (c-2) is practiced to determine vacuum strength in inches of Hg.

7. A method according to claim 6, wherein the flow ability factor (K) is determined according to $K=Q/\sqrt{\Delta P}$, where Q is the vacuum flow in SCFM and $\Delta P$ is the vacuum strength in inches of Hg.

8. A method according to claim 1, wherein the vacuum strength measurement device comprises at least one of a vacuum flow measurement device and a vacuum gauge.

9. A method of determining a vacuum strength requirement for a vacuum producer system serving a plurality of vacuum devices, the method comprising:
   (a) measuring vacuum performance for existing vacuum devices with a vacuum strength measurement device;
   (b) measuring sealed vacuum strength with the vacuum strength measurement device;
   (c) determining a flow ability factor based on the vacuum performance and the sealed vacuum strength; and
   (d) calculating an amount of vacuum strength required to match a target vacuum performance based on the flow ability factor determined in step (c).

10. A method according to claim 9, wherein the vacuum strength measurement device comprises a vacuum flow measurement device, wherein step (a) is practiced by attaching the vacuum flow measurement device with an open end, and wherein step (b) is practiced by attaching the vacuum flow measurement device with a closed end.

11. A method according to claim 9, wherein step (a) is practiced to determine vacuum flow as standard cubic feet per minute (SCFM).

12. A method according to claim 11, wherein step (b) is practiced to determine vacuum strength in inches of Hg.

13. A method according to claim 12, wherein the flow ability factor (K) is determined according to $K=Q/\sqrt{\Delta P}$, where Q is the vacuum flow in SCFM and $\Delta P$ is the vacuum strength in inches of Hg.

14. A method according to claim 9, wherein the vacuum strength measurement device comprises at least one of a vacuum flow measurement device and a vacuum gauge.

* * * * *